US006403327B1

(12) United States Patent
Liao et al.

(10) Patent No.: US 6,403,327 B1
(45) Date of Patent: *Jun. 11, 2002

(54) DIAGNOSTIC METHOD USING EXPRESSION OF MN/CA9 PROTEIN IN ASCUS PAP SMEARS

(75) Inventors: Shu-Yuan Liao, Anaheim; Eric J. Stanbridge, Corona del Mar, both of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/572,756

(22) Filed: May 16, 2000

Related U.S. Application Data

(63) Continuation-in-part of application No. 09/461,938, filed on Dec. 15, 1999.
(60) Provisional application No. 60/147,556, filed on Aug. 5, 1999.

(51) Int. Cl.[7] .................. G01N 33/574; G01N 33/53; G01N 33/567; A61K 7/025; C07K 16/00
(52) U.S. Cl. .................. 435/7.23; 435/7.1; 435/7.2; 424/64; 530/387.1
(58) Field of Search .................. 530/387.1; 435/7.1, 435/7.2, 7.23; 424/64

(56) References Cited

U.S. PATENT DOCUMENTS

| 5,955,075 A | 9/1999 | Zavada et al. |
| 5,981,711 A | 11/1999 | Zavada et al. |
| 6,004,535 A | 12/1999 | Zavada et al. |
| 6,027,887 A | 2/2000 | Zavada et al. |
| 6,051,226 A | 4/2000 | Zavada et al. |
| 6,069,242 A | 5/2000 | Zavada et al. |
| 6,093,548 A | 7/2000 | Zavada et al. |
| 6,204,370 B1 | 3/2001 | Zavada et al. |
| 6,297,041 B1 | 10/2001 | Zavada et al. |
| 6,297,051 B1 | 10/2001 | Zavada et al. |

OTHER PUBLICATIONS

Liao et al., Identification of the MN Antigen as a Diagnostic Biomarker of Cervical Intraepithelial Squamous and Glandular Neoplasia and Cervical Carcinomas, American Journal of Pathology, vol. 145, No. 3, 1994.*
Liao et al., Expression of MN Antigen in Cervical Papanicolaou Smears is an early Diagnostic Biomarker of General Cervical Dysplasia, Cancer Epidemeology, Biomarkers & Prevention, vol. 5, 549–557, 1996.*
Stanbridge, Eric, A protein antigen holds promise for better cervical cancer detection, UC Irvine researcher reports, UCI News, Mar. 23, 1998.
Lett, David N., Transatlantic antigen enhances reliability of cervical cancer pap test: clinical trials pending, BioWorld Today Archives, Mar. 24, 1998.
Cervical marker can help resolve ambiguous pap smears, Diagnostic Intelligence, vol. 10, No. 5, May 1998, p. 2, col. 1.
New Tests Unveiled that Detect Cancer, San Francisco Chronicle, Mar. 27, 1998, p. A8.
New Test Could End Pap Smear 'Gray Area', Los Angeles Times, Mar. 24, 1998, p. B4.

* cited by examiner

*Primary Examiner*—Sheela Huff
*Assistant Examiner*—Jennifer Hunt
(74) *Attorney, Agent, or Firm*—Fulbright & Jaworski

(57) ABSTRACT

Determining the presence of cancerous or pre-cancerous cervical lesions from ASCUS-diagnosed Pap smear cells by observing the distribution of MN/CA9 antigen expressed on atypical or normal cells and diagnosing (a) significant lesions when MN/CA9 antigen is observed on atypical cells, (b) low grade lesions when MN/CA9 antigen is absent from atypical cells but is present on normal endocervical cells, and (c) a benign condition when MN/CA9 antigen is absent from both atypical cells and normal endocervical cells.

5 Claims, 3 Drawing Sheets

DIAGNOSTIC METHOD USING EXPRESSION OF MN/CA9 PROTEIN IN ASCUS PAP SMEARS

CROSS REFERENCE TO RELATED APPLICATIONS

This application is a continuation-in-part of application Ser. No. 09/461,938, filed Dec. 15, 1999 which, in turn, claimed the benefit of Provisional Patent Application No. 60/147,556, filed Aug. 5, 1999.

BACKGROUND OF THE INVENTION

Cervical cancer is one of the most common malignancies in women worldwide, second only to breast cancer in both incidence and mortality. In the United States, both morbidity and mortality have decreased dramatically since the 1940s, when the Papanicoleau (Pap) smear test was introduced ("NIH Consensus Statement (1) Cervical Cancer", infra). Despite aggressive screening there are still approximately 16,000 new cases of cervical cancer per year, and approximately 5,000 deaths. Although part of the reason for this level of morbidity and mortality is due to the fact that some women fail to have regular routine Pap smears; another reason is that Pap smears are relatively frequently misdiagnosed. This includes inherently high false negative rates and inconsistent cytological reporting systems (Koss, L. G., 1989, infra); Yobs, A. R., et al, infra; and Koss, L. G., 1993, infra).

A major problem has been that since the introduction of Pap smear screening, the descriptive terminology for cervical cytology has been variable and confusing (Jones, H. W., infra). In 1988, a NCI-sponsored workshop developed new terminology for Pap smear screening that was intended to clarify the system of cytologic scoring, which resulted in "The 1988 Bethesda System for reporting cervical/vaginal cytological diagnoses" (National Cancer Institute Workshop, infra). This was further modified in 1991 (Broder, S., infra). The Bethesda System (TBS), as it became known, introduced the categories of "atypical squamous cells of undetermined significance" (ASCUS), and "atypical glandular cells of undetermined significance" (AGCUS or AGUS). In our previous patent application Ser. No. 09/461,930, we provided an effective method for dealing with the AGUS diagnostic category. However, the ASCUS "diagnostic" category remains problematic for the cytopathologist and practicing physician.

The original intent was to use the ASCUS designation as a category of squamous cell abnormality for cases not diagnostic of a reactive/inflammatory, dysplastic, or neoplastic condition (Boemer, S. L., et al, infra). Unfortunately, the ASCUS diagnosis does not identify a specific clinical entity, and reflects one of the inherent limitations of the Pap screening procedure. To add to this problem, the diagnosis of ASCUS rapidly grew popular in testing laboratories and has approached frequencies up to 10% of all Pap test results! The ASCUS diagnosis has been termed "a wastebasket category in some labs" and "an I-don't-know category" ("Getting a handle on ASCUS; a new clinical trial could show how", JNCI 87(No. 7), Jun. 7, 1995. Currently, it is recommended that the diagnosis of ASCUS should be qualified additionally, to include ASCUS-favor reactive, ASCUS-not otherwise specified (NOS), or ASCUS-favor squamous intraepithelial lesion (SIL) (Kurman, R. J., Hanson, et al, infra). However, these distinctions have been controversial; the uncertainty associated with a diagnosis of ASCUS has been well documented (Boemer, S. L., et al, infra).

An ASCUS diagnosis presents a serious clinical challenge. Up to one third of women who receive a diagnosis of ASCUS harbor significant lesions. Moreover, more than one third of HSILs found in screening patients are identified from ASCUS Pap test results. However, this also means that two thirds of women who receive a Pap smear diagnosis of ASCUS do not harbor a cervical lesion.

No satisfactory adjunct test has previously been identified that serves to complement the diagnosis of ASCUS, thereby aiding in identifying the presence of a significant lesion. However, screening for the presence of high-risk types of human papillomavirus (HPV) in Pap smear specimens has helped to identify those women with underlying HSIL; see Sherman, M. E., et al, infra; and Hatch, K. D., et al, infra. Molecular and epidemiologic evidence has accrued that indicates that infection with high-risk types of HPV is a major risk factor for invasive cervical cancer; see zur Hausen, H., infra. The association, however, is not absolute because a small proportion of cytologically negative women have detectable high-risk HPV DNA. Conversely, some HSILs are HPV negative; see Boemer, S. L., et al, infra. A large multicenter clinical trial (the ALTS study), designed to determine the utility of HPV DNA testing, is currently in progress, sponsored by the National Cancer Institute.

Recent studies have indicated that expression of proliferation-associated proteins, e.g. Ki67 and PCNA, may also serve as useful indicators of the presence of dysplastic lesions; see Bulten, J., et al, infra; and Mittal, K. R., et al, infra. However, no specific analyses have been applied to Pap smear specimens.

The essence of the problem is that ASCUS diagnoses will include a significant fraction of cases of low grade intraepithelial neoplasia (CINI), also termed low grade squamous intraepithelial lesion (LSIL). Only a small percentage of LSILs will progress to significant lesions, i.e. high grade squamous intraepithelial lesion (HSIL, also designated CIN II, III) and carcinoma in situ (CIS). Another serious problem is that the incidence of high grade lesions may be as high as 10% in patients who receive an ASCUS diagnosis of their cervical/vaginal smear—a total of approximately 2–3 million per year (Davey, D. D., et al, infra). Because of the current legal climate in the United States, the majority of ASCUS diagnoses are aggressively followed up with colposcopy and selected biopsy. Although colposcopy for all patients with atypical smears identifies those patients with SIL, it carries substantial personnel and financial costs, and subjects some patients to unnecessary invasive procedures that carry an element of risk.

It would be highly desirable to provide a reliable supplementary test that will allow for further discrimination of ASCUS diagnoses, identifying those patients with significant lesions, and providing a better prognostic picture of which LSILs are destined to progress versus regress.

One approach is to use a surrogate biomarker. We previously identified such a candidate biomarker—the MN/CA9 antigen (Liao, S. Y., Brewer, C., et al, infra); and Liao, S. Y., and Stanbridge, E. J., et al, infra). Several years ago, we found that this antigen is expressed on the plasma membrane surface of virtually all cervical carcinomas, irrespective of their provenance (Liao, S. Y., Brewer, C., et al, et al, infra). The gene encoding MN/CA9 was cloned and, at the time, was novel (Pastorek, J., et al, infra). It has now been recognized as a member of the carbonic anhydrase family. Recent studies have suggested that, in addition to carbonic anhydrase activity, MN/CA9 may function as an adhesion protein and preliminary evidence suggests it may have transforming activity in mouse NIH3T3 assays (Zavada, J., et al, infra).

In a study of over 300 Pap smears, representing the complete spectrum of benign and neoplastic cervical lesions, we showed that high levels of MN/CA9 were expressed in all cases of AIS and adenocarcinoma, in more than 90% of cases of cervical squamous cell carcinoma and, to a lesser degree, in SILs. This study concluded the following: 1) MN/CA9 expression in exfoliative cells recapitulates MN/CA9 expression in the tissue sections; 2) diffuse strong MN/CA9 immunoreactivity of cells in the cervical smears always appears to be associated with dysplasia, regardless of whether the positive cells have the cytologic appearance of normal or atypical endocervical cells or dysplastic cells; and 3) virtually all dysplastic glandular cells in the cytologic smears express MN/CA9 protein. Thus, MN/CA9 protein expression in exfoliative endocervical cells would appear to be an important diagnostic biomarker of glandular dysplasia, AIS, invasive adenocarcinoma, and/or SIL (Liao, S. Y, and Stanbridge, E. J., etal, infra).

As discussed above, the cytologic diagnoses of ASCUS and AGUS are particularly vexing for gynecologists—leaving them in a quandary as to the optimal regimen of further examination/treatment. In our prior, co pending patent application, we demonstrated that the combination of cytology and MN/CA9 expression in AGUS—diagnosed Pap smears allows for the identification of those patients harboring significant lesions (CIN II, III and/or AIS/CA). The results described in the application are so promising that a clinical trial has been initiated under the auspices of the National Cancer Institute and the Multicenter Gynecologic Oncology Group.

BRIEF SUMMARY OF THE INVENTION

The present invention provides an adjunct test to the conventional Papanicolaou (Pap) smear, that will allow for identification of those patients with a diagnosis of ASCUS who harbor a significant lesion (high grade squamous intraepithelial lesion (HSIL) and/or carcinoma). The invention proceeds by immunostaining Pap smears and corresponding histologic biopsies for expression of the MN/CA9 antigen. More specifically, Pap smears with a diagnosis of ASCUS are immunostained for expression of the MN/CA9 antigen. The presence of MN/CA9 immunostaining of the Pap smears is correlated with the histologic diagnosis of the corresponding biopsy. Those ASCUS-diagnosed Pap smears with specific MN/CA9 immunostaining correspond to biopsies that contain SIL and/or carcinoma (CA). The pattern of immunostaining (focal or diffuse staining of atypical cells versus normal cells only) discriminates between biopsies that contain low grade squamous intraepithelial lesion (LSIL) (immunostaining of normal cells only) versus a high grade squamous intraepithelial lesion (HSIL) and/or CA (focal or diffuse staining of atypical cells).

DETAILED DESCRIPTION OF THE INVENTION

Figure 1A:
FIG. 1 provides comparative illustrations of original Pap stained smears (A and D), MN/CA9 immunostained smears (B and E) and re-stained Pap smears after Immunostaining (C and F)

The method of the present invention entails examination of the levels and distribution of expression of MN/CA9 antigen to confirm diagnoses obtained by cytological examinations, e.g., Pap smears, when observing atypical squamous cells of undetermined significance (ASCUS). A positive result serves as an early marker of dysplasia even in the absence of its clinical manifestations. The MN/CA9 antigen has shown to be useful in identifying cervical dysplasia/carcinorna and, as shown in our previous patent application Ser. No. 09/461,930, provides an effective method for dealing with the atypical glandular cells of undetermined significance (AGUS) diagnostic category. Our studies now indicate that MN/CA9 expression will provide a similar discriminator of associated significant lesions for the ASCUS category.

We have examined 82 specimens with a Pap smear diagnosis of ASCUS that have a corresponding tissue biopsy with a histologic diagnosis. As illustrated in Table 1, there were 44 specimens that stained positively for MN/CA9 expression. Of these, the majority (n=35) had an LSIL-diagnosed tissue biopsy. Only one MN/CA9 positive smear had a benign tissue biopsy.

TABLE 1

The correlation between MN/CA9 immunoreactivity in ASCUS-diagnosed Pap smears and squamous intraepithelial lesions (SILs) in tissue biopsies.

| MN/CA9 immunoreactivity ASCUS (n = 101) | Histologic diagnosis | | | |
|---|---|---|---|---|
| | HSIL (CIN II, III) | LSIL (CIN I) | ATYPIA | BENIGN |
| Positive stain (n = 44) | 5 | 35 | 3 | 1 |
| Diffuse stain (n = 19) | 2 | 17 | 0 | 0 |
| No stain (n = 38) | 0 | 2* | 2 | 34 |

*Cervix shows minimal condyloma

In recent years, it has become relatively common practice among cytopathologists to subcategorize ASCUS diagnoses into ASCUS-favor reactive, ASCUS-not otherwise specified (NOS), and ASCUS favor SIL. A similar subcategorization is also used for AGUS-diagnosed Pap smears. In a limited pilot study or such subcategorized ASCUS diagnoses we, again, found that MN/CA9 expression is significantly associated with the presence of SIL (HSIL and LSIL) in the tissue biopsies (Table 2).

Our data clearly indicates that ASCUS diagnoses may be aided-in the sense of predicting the presence of an SIL-by the identification of MN/CA9 immunopositivity in the Pap smear.

TABLE 2

An analysis of MN/CA9 immunoreactivity in ASCUS-diagnosed Pap smears, representing ASCUS subcategories. Histologic Diagnosis and MN/CA9 antigen expression No. of cases (No. MN/CA9 positive)

| ASCUS (n = 33) | | HSIL (CIN II, III) | LSIL (CIN I) | ATYPIA | BENIGN |
|---|---|---|---|---|---|
| Favor Reactive | (n = 4) | 0 | 0 | 1(1) | 3(0) |
| N.O.S. | (n = 20) | 2(2) | 9(8)* | 3(1) | 6(1) |
| Favor SIL | (n = 9) | 3(3) | 2(2) | 1(1) | 3(0) |

*One MN/CA9-negative LSIL case in which the cervix shows minimal condyloma

To the best of our knowledge, we are the first to evaluate MN/CA9 expression as a useful biomarker for determining whether a significant cervical lesion is present in women who receive a Pap test diagnosis of ASCUS. Other investigators have independently confirmed our earlier observations of the association of MN/CA9 expression and the presence of cervical dysplasia and/or carcinoma in tissue specimens; see Costa, M. J.(1996), infra; and Costa, M. J., et al (1995), infra.

EXAMPLES

Specimen Collection

Figure 1B:
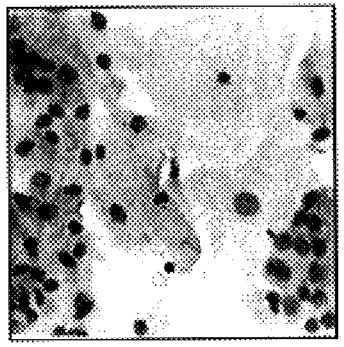
Figure 1C:
Figure 1D:
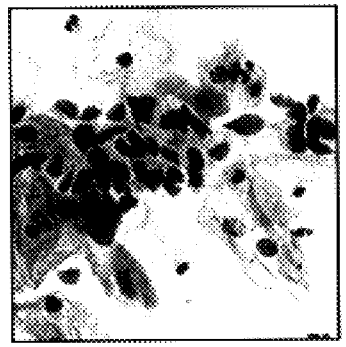
Figure 1F:
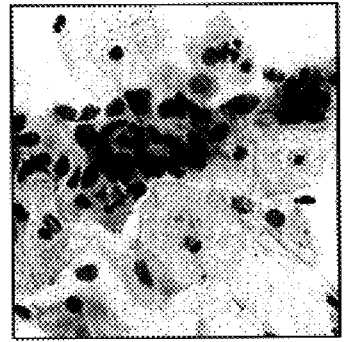
Figure 1G:
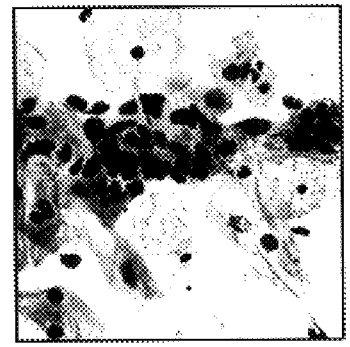

Clinical specimens are accessed from archival material, derived from routine clinical practice, a method of resource acquisition we have used successfully for all of our previous studies; see Liao, S. Y., Brewer, C., et al, supra; and Liao, S. Y, and Stanbridge, E. J., supra). The Pap smear specimens are a combination of conventional smears that have been spray fixed and Thin Prep specimens. All of the immunostained Pap smears are destained and restained with Papanicolaou stain, and kept in a permanent file. Examples of this process are shown in FIG. 1 which provides comparative illustrations of original Pap stained smears (A and D), MN/CA9 immunostained smears (B and E) and re-stained Pap smears after Immunostaining® and F). The re-stained Pap smears still retain the cytologic property as the original smears.

Ascus Subcategories

Of a total of 726 ASCUS cases (all with histologic confirmation) available to us, 149 were ASCUS-favor reactive, 416 ASCUS-NOS, and 161 ASCUS-favor LSIL. Those patients with a diagnosis of ASCUS-favor LSIL receive an immediate colposcopy and histologic diagnosis. Patients in the other two categories receive a repeat Pap test. If the repeat diagnosis is ASCUS or LSIL, the patient is referred to colposcopy.

Immunostaining

MN/CA9: A mouse monoclonal antibody (MAb), designated M75, is used (Liao, S. Y., Brewer, C., et al, supra). It recognizes the proteoglycan domain of the MN/CA9 peptide. The MN/CA9 antigen is remarkably robust and survives Papanicolaou staining of Pap smears (thereby allowing for destaining of routine Pap smears followed by immunostaining with the M75 MAb), as well as fixation and paraffin embedding of tissues (Liao, S. Y., Brewer, C., et al, supra; and Liao, S. Y, and Stanbridge, E. J., supra).

For tissue sections, five micron sections of paraffin-embedded tissues are deparaffinized. The endogenous peroxidase is blocked by incubating the slides in a solution of 2.5% hydrogen peroxide in methanol for 45 minutes. The slides are then incubated with the appropriate blocking serum (5% normal horse serum in PBS) for 20 minutes. All incubations are performed at room temperature in humidified chambers. The slides are then incubated with ascites fluid-derived primary antibody M75 (1:10,000 dilution in PBS-containing 0.1% bovine serum albumin) for 60 minutes, then a 30 minute incubation with secondary biotinylated horse antimouse immunoglobulin G antibody (1:200 dilution in PBS), followed by incubation with avidinbiotin peroxidase complexes (ABC Elite) for 30 minutes (Vector Laboratories, Burlingame, Calif. ). Diaminobenzidine tetrahydrochloride (DAB) is used as chromagen (Sigma Chemical Co., St. Louis, Mo.). After treatment, the sections are washed with distilled $H_2O$, counterstained with hematoxylin, and mounted with permount.

Duplicate deparaffinized sections of selected samples are also pretreated with microwaves. In this regard, the sections are rehydrated in 10 mmol/L citric acid monohydrate solution (pH 6.0), placed in the microwave oven and subjected to 2×5 minute exposures at the high setting. The slides are allowed to cool and then are rinsed with distilled $H_2O$, and PBS. The slides are then processed for staining as described above. Known positive and negative specimens are included in each staining run. For cervical smears, the routine Pap-stained smears are first decolorized with 1% acid alcohol and rinsed with distilled water. The smears are then immunostained following the procedure described above.

The specificity of immunostaining is identified by the presence of a brown reaction product, predominantly on the plasma membrane (see FIG. 1). The patterns of immunostaining—focal versus diffuse and normal cells only versus atypical cells—are identified and recorded.

The metaplastic squamous cell, reserve cell, and columnar cell constitute the cell population that we define as normal endocervical cells (ECs). Any MN/CA9 immunoreactive parabasal dyskeratotic cells and/or cells that morphologically deviate from normal ECs are considered as atypical cells or cell clusters. The nuclei of those atypical cells are, in general, 2–3 times larger than normal ECs and exhibit significant hyperchromasia with an increased nuclear/cytoplasmic ratio.

Figure 2A:
FIG. 2 shows MN/CA9 immunoreactivity in conventional Pap smears (panels A, D and G) and Thin Prep smears (panels B, E and H) with cytologic diagnosis of ASCUS, and the corresponding Histology.
Figure 2B:
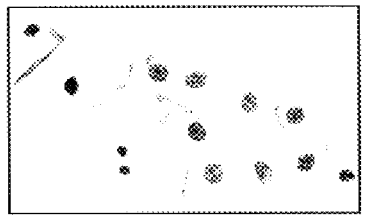
Figure 2C:
Figure 2D:
Figure 2E:
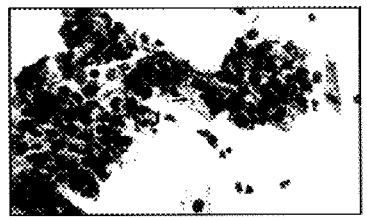
Figure 2F:
Figure 2G:
Figure 2H:
Figure 2I:

Referring to FIG. 2, in panels A and B, no immunoreactivity is seen. The cervix has benign histology (panel C). In panels D and E, diffuse positivity is seen in the majority of normal endocervical cells, and low-grade dysplasia (LSIL/CIN I) is identified in the cervical tissue (panel F). In panels G and H, MN/CA9 immunoreactivity is seen in atypical cells, characterized by increased nuclear/cytoplasmic ratio and nuclear hyperchromasia. The cervical tissue section contains a high-grade lesion (CIN III, panel 1). (Magnification 400×) shows a spectrum of squamous and glandular alterations, illustrating the criteria for diagnosis of atypia, preneoplastic and neoplastic lesions: Panel A is a normal cervix showing orderly arrangement of squamous and glandular epithelium, Panel B is an example of atypical squamous metaplasia (left) and reserve cell proliferation (right), Panel C is an example of glandular atypia with epithelial stratification, Panels D and E illustrate LSIL and HSIL, respectively, and Panel F is an example of AIS (Magnification: A 100×, B-F 200×);

Ki67

Figure 3A:
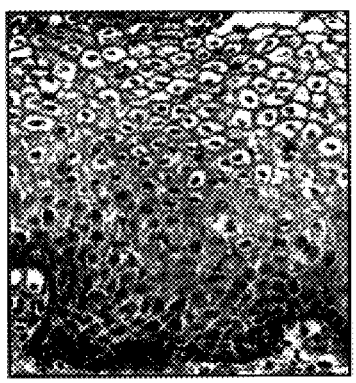
FIG. 3 shows the comparative illustrations of Ki 67 and MN/CA9 expression in benign and dysplastic cervical tissues, and the corresponding histology.
Figure 3B:
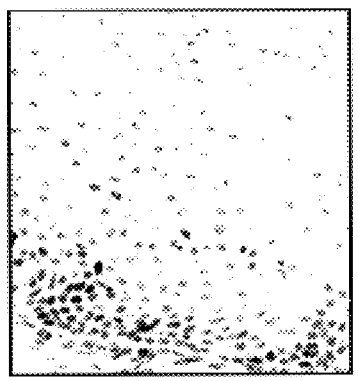
Figure 3C:
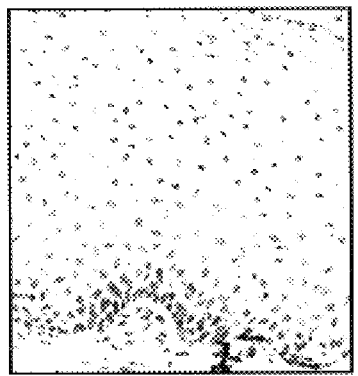
Figure 3D:
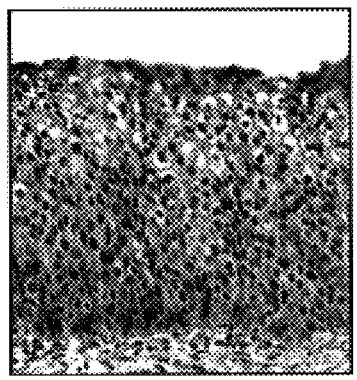
Figure 3E:
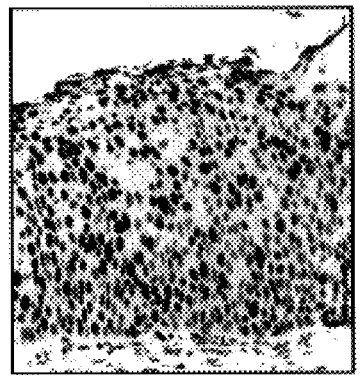
Figure 3F:
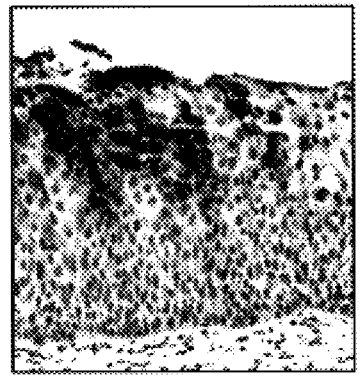

The Ki67 mouse monoclonal antibody is obtained from commercial sources (e.g. Immunotech Corp., Maine), and is used according to the manufacturer's protocol. Ki67 immunostaining is performed on tissue sections. The immunostaining pattern is used as an index of proliferation, to confirm the histologic diagnosis (Bulten, J., supra) and to correlate with MN/CA9 expression. We have found that immunostaining of tissue sections works well, using the MN/CA9 protocol. Examples of Ki67 immunostaining are shown in FIG. 3 where, in benign cervix (A), the Ki 67 positivity is restricted to the basal cell layer (B) and no MN/CA9 immunoreactivity is seen (C). In contrast, the dysplastic cervix (D, CIN III ) shows Ki 67 nuclear staining in all layers of dysplastic cells (E), and there is diffuse MN/CA9 immunoreactivity in the corresponding section (F). (Magnification 200×). FIG. 3 shows staining patterns of MN/CA9 immunoreactivity in AGUS Pap smears.

The pattern of immunostaining (focal or diffuse staining of atypical cells versus normal cells only) discriminates between biopsies that contain low grade squamous intraepithelial lesion (LSIL) (immunostaining of normal cells only) versus a high grade squamous intraepithelial lesion (HSIL) and/or CA (focal or diffuse staining of atypical cells).

Study Population

Our study population is derived from women who have received a Pap smear diagnosis of ASCUS. All cases studied are accompanied by a histologic diagnosis, based upon a tissue biopsy taken at the time of the initial ASCUS diagnosis or following a repeat Pap smear diagnosis that is abnormal or ASCUS, specifically. Archival material is used for all of the study specimens. Both Pap smears and corresponding cervical tissue specimens are derived from routine diagnostic material. Smears and tissue sections are obtained from the same patient. In those cases where a routine conventional. Pap smear specimen is used, the immunostained smear is destained and restained with Papanicolaou stain.

Basically, there are two categories of patients with an ASCUS diagnosis:

1) Those patients who receive a Pap smear diagnosis of ASCUS-favor SIL. These patients receive an immediate colposcopic examination and cervical biopsy and/or curettage. In this group we are able to directly ascertain the correlation between MN/CA9 expression and the presence of lesions (SIL and/or CA).

2) Those patients who receive a Pap smear diagnosis of ASCUS-favor reactive or ASCUS-NOS. These patients are followed-up with repeat Pap smear(s). If the patient receives an SIL or persistent ASCUS diagnosis then a colposcopic examination and cervical biopsy and/or curettage are performed, in 3–12 months. Several results are possible, namely:

|  |  | MN/CA9gimmunoreactivity | Biopsy |
| --- | --- | --- | --- |
| Possibility 1 | 1st Pap smear | + | N.D. |
|  | 2nd Pap smear | + | SIL/CA |
| Possibility 2 | 1st Pap Smear | − | N.D. |
|  | 2nd Pap smear | − | Benign |
| Possibility 3 | 1st Pap Smear | − | N.D. |
|  | 2nd Pap smear | + | SIL/CA |

In a small study we have found examples of Possibilities 1 and 2, but not Possibility 3. This is consistent with the notion that the presence of a significant lesion or LSIL would be accompanied by positive MN/CA9 expression. Furthermore, the likelihood that one would encounter the situation where the progression from benign →SIL would occur within the 3–12 month follow-up period would be very slight. In a retrospective study of a small number of cases (n=20) we found that when there is a conversion from a within-normal-limits (WNL) Pap smear diagnosis to ASCUS over a time span of 1–3 years, and the follow-up ASCUS biopsy is diagnosed as LSIL or HSIL, both ASCUS Pap smears are MN/CA9 immunopositive, whereas the original WNL Pap smear was MN/CA9 negative.

BIBLIOGRAPHY

The following references are incorporated herein by reference:

Boemer, S. L., and Katz, R. L. On the origins of "Atypical Squamous Cells of Undetermined Significance": the evolution of a diagnostic term. Adv. Anatom. Path. 4:221–232, 1997.

Broder, S. The Bethesda System for reporting cervical/vaginal cytologic diagnoses: report of the 1991 Bethesda Workshop, JAMA 267:1892, 19,02.

Bulten, J., van der Laak, J. A., Gemmink, J. H., Pahiplatz, M. M., de Wilde, P. C., and Hanselaar, A. G. MIB 1, a promising marker for the classification of cervical intraepithelial neoplasia. J. Pathol. 178(3):268–273, 1996.

Costa, M. J. MN and Ki67 (MIB-1) in uterine cervix carcinoma: novel biomarkers with divergent utility. Hum. Pathol. 27:17–19, 1996.

Costa, M. J., Ndoye, A., and Trelford, J. D. MN protein immunolocalization in uterine cervix carcinoma with glandular differentiation. Int. J. Surg. Pathol. 3:73–82, 1995.

Davey, D. D., Naryshkin, S., Nielsen, M. D., and Kline, T. S. Atypical squamous cells of undetermined significance: interlaboratory comparisons and quality assurance monitors. Diagn. Cytopathol. 11:390–396, 1994.

Dunn, G., and Everitt, B. Clinical problems and statistical solutions. In Clinical Biostatistics, New York Halstead Press. pp1–32, 1995.

Editorial. Getting a handle on ASCUS; a new clinical trial could show how. JN 87(No. 7), Jun. 7, 1995.

Emmert-Buck, M. R., Bonnet, R. F., Smith, P. D., Chuaqui, R. F., Zhuang, Z., Goldstein, S. R., Weiss, R. A., and Liotta, L. Laser capture microdissection. Science. 274:998–1001, 1996.

Hatch, K. D., Schneider, A., and Abdel-Nour, M. W. An evaluation of human papillomavirus testing for intermediate- and high-risk types as triage before colposcopy. Am. J. Obstet Gynecol. 172:1150–1157, 1995.

Herrington, C. S., Evan, M. F., Gray, W., and McGee J. O'D. Morphological correlation of human papillomavirus infection of matched cervical smears and biopsies from patients with persistent mild cervical cytological abnormalities. Hum. Pathol. 26:951–955, 1995.

Jones, H. W. Impact of the Bethesda System. Cancer 76:1914–1918, 1995.

Koss, L. G., "The Papanicolaou tests for cervical cancer detection: a triumph and a tragedy", JAMA. 261:737–743, 1989.

Koss, L. G. Diagnostic accuracy in cervicovaginal cytology. Arch. Pathol. Lab. Med. 117:1240–1242,1993.

Kurman, R. J., Hanson, D. E., Herbst A. L., and Noller K. L. Interim guidelines R management of abnormal cervical cytology, JAMA 271:1866–1869, 1994.

Kurman, R. J., and Solomon, D. The Bethesda system for reporting cervical/vaginal cytologic diagnoses. Definitions, criteria and explanatory notes for terminology and specimen adequacy. New York: Springer-Verlag. pp,30–43, 1994.

Larson, A. A., Liao, S. Y., Stanbridge, E. J., Cavenee, W. K., and Hampton, G. M. Genetic alterations accumulate during cervical tumorigenesis and imply a common origin for multifocal lesions. Cancer Research 57:4171–4176, 1997.

Liao, S. Y., Brewer, C., Zavada, J., Pastorek, J., Pastorekova, S., Marietta, A., Berman, M. L., DiSala, P. J., and Stanbridge, E. J. Identification of the MN antigen as a diagnostic biomarker of cervical intraepithelial squamous and glandular neoplasia and cervical carcinomas. Am. J. Pathol., 145:598–609, 1994.

Liao, S. Y, and Stanbridge, E. J. Expression of the MN antigen in cervical Papanicolaou smears Is an early diagnostic biomarker of cervical dysplasia. Canc. Epid. Biom. Prev., 5:549–557, 1996.

Mashal, R. D., Lester, S. C., and Sklar, J. Clonal analysis by study of X chromosome inactivation in formalin-fixed, paraffin-embedded tissue. Cancer Res. 53:4676–4679, 1994.

McNemar, Q. Psychological statistics (2 nd Ed.) New York: Wiley, 1955.

Mittal, K. R., Demopoulos, R. I., and Goswarni, S. Proliferating cell nuclear antigen (Cyclin) expression in normal and abnormal cervical squamous epithelial. Am. J. Surg. Pathol. 7:117–122, 1993.

National Cancer Institute Workshop. The 1988 Bethesda System for reporting cervical/vaginal cytological diagnoses. JAMA 262:931–934, 1989.

NIH Consensus Statement (1) Cervical Cancer. 14:1–18, 1996. Koss, L. G. The Papanicolaou tests for cervical cancer detection: a triumph and a tragedy. JAMA. 261:737–743, 1989.

Pastorek, J., Pastorekova, S., Callebaut, I., Morrion, J. P., Zelnik, V., Opavsky, R., Zatovicova, M., Liao, S., Portelle, D., Stanbridge, E. J., Zavada, J., Burny, A., and Kettmarm, R. Cloning and characterization of MN, a human tumor-associated protein with a domain homologous to carbonic anhydrase and a putative helix -loop-helix DNA binding segment. Oncogene 9:2877–2888, 1994.

Pastorekova, S., Zavadova, Z., Kostal, M., Babusikova, O., and Zavada J. A novel quasi-viral agent, MaTu, is a two-component system. Virology 187–620–626, 1992.

Poljak, M., Brencic, A., Seme, K., Vince, A., and Marin I. J. Comparative evaluation of first- and second-generation Digene Hybrid Capture assays for detection of human papillomaviruses associated with high or intermediate risk cervical cancer. J. Clin. Microbiol. 37:796–797, 1999.

Resnick, R. M., Cornelissen, M. T., Wright, D. K., Eichinger, G. H., Fox, H. S., ter Schegget, J., and Manos, M. M. Detection and typing of human papillomavirus in archival cervical cancer specimens by DNA amplification with consensus primers. J. Natl. Cancer Inst. 82:1477–1484, 1990.

Sherman, M. E., Tabarra, S. O., Scott, D. R., Kurman, R. J., Glass, A. G., Manos, M. M., Burk, R. D., Rush, B. B., and Schiffman, M. "ASCUS, rule out HSIL": cytologic features, histologic correlates, and human papillomavirus detection. Mod.Pathol. 12:335–342, 1999.

Yobs, A. R., Swanson, R. A., and Lamotte, L. C. Laboratory reliability of the Papanicolaou smear. Obstet. Gynecol. 65:235–244, 1985.

Zavada, J., Zavadova, Z., Pastorekova, S., Ciampor, F., Pastorek, J., and Zelnik, V. Expression of MaTu-MN protein in human tumor cultures and in clinical specimens. Int. J. Cancer. 54:268–274, 1993.

zur Hausen, H., Molecular pathogenesis of cancer of the cervix and its causation by specific human papillomavirus types. Curr. Topics Microbiol. Immunol. 186:131–156, 1994.

We claim:

1. A method for determining the presence or absence of cancerous or pre-cancerous cervical lesions from Pap smear cells that have been cytologically diagnosed as atypical squamous cells of undetermined significance (ASCUS) under the Bethesda System of terminology, said Pap smear including atypical and normal endocervical cells, said method comprising:
   (A) subjecting said ASCUS-diagnosed Pap smear cells to a procedure whereby MN/CA9 antigen is detected;
   (B) observing the distribution of MN/CA9 antigen detected on atypical or normal cells of said ASCUS cytologically diagnosed Pap smear cells; and
   (C) classifying the ASCUS cytologically diagnosed pap smear cells into diagnostic categories based on the distribution of MN/CA9 antigen observed on said ASCUS cytologically diagnosed pap smear cells, wherein;
      (1) the presence of focal or diffuse MN antigen on said atypical cells is diagnostic of significant lesions including adenocarcinoma, invasive carcinoma (CA), or high grade squamous intraepithelial lesions (HSIL),
      (2) the absence of MN antigen on said atypical cells and the presence of MN antigen on said normal endocervical cells is diagnostic of LSIL and/or atypia, and
      (3) the absence of MN antigen on said atypical cells and on said normal endocervical cells is diagnostic of a benign condition, atypia or minimal condyloma.

2. The method of claim 1 wherein said Pap smear cells that have been sub-categorized as ASCUS-favor reactive, ASCUS-not otherwise specified (NOS), and ASCUS favor SIL, and wherein the absence of MN/CA9 detection on Pap smear cells that have been sub-categorized as ASCUS-favor reactive or NOS further confirms a benign condition.

3. The method of claim 1, wherein said MN antigen comprises a characterizing fraction of an MN/CA9 protein, said characterizing fraction comprising at least one antigenic determinant or immunoreactive epitope of the MN/CA9 protein, which binds detectably to an anti-MN/CA9 antibody.

4. The method of claim 1, wherein said expression is detected by immunohistochemistry.

5. The method of claim 1 wherein said ASCUS-diagnosed Pap smear cells are without cytologically diagnosed SIL.

* * * * *

(12) EX PARTE REEXAMINATION CERTIFICATE (5267th)
United States Patent
Liao et al.

(10) Number: US 6,403,327 C1
(45) Certificate Issued: *Feb. 7, 2006

(54) DIAGNOSTIC METHOD USING EXPRESSION OF MN/CA9 PROTEIN IN ASCUS PAP SMEARS

(75) Inventors: Shu-Yuan Liao, Anaheim, CA (US); Eric J. Stanbridge, Corona del Mar, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Reexamination Request:
No. 90/006,319, Jul. 3, 2002

Reexamination Certificate for:
Patent No.: 6,403,327
Issued: Jun. 11, 2002
Appl. No.: 09/572,756
Filed: May 16, 2000

Related U.S. Application Data

(63) Continuation-in-part of application No. 09/461,938, filed on Dec. 15, 1999, now Pat. No. 6,379,907.
(60) Provisional application No. 60/147,556, filed on Aug. 5, 1999.

(51) Int. Cl.
*G01N 33/574* (2006.01)
*G01N 33/53* (2006.01)
*G01N 33/567* (2006.01)
*A61K 7/025* (2006.01)
*C07K 16/00* (2006.01)

(52) U.S. Cl. .......... 435/7.23; 435/7.1; 435/7.2; 424/64; 530/387.1
(58) Field of Classification Search .......... None
See application file for complete search history.

(56) References Cited

U.S. PATENT DOCUMENTS 6,297,051 B1 * 10/2001 Zavada et al.

OTHER PUBLICATIONS

Liao and Stanbridge, Cancer Epidemiology, Biomarkers & Prevention 5(7):549–557, 1996.*

Altman et al, The Cancer Dictionary, 1992, p. 118 and p. 259.*

Abstract of the 1997 Annual Meeting of the United States and Canadian Academy of Pathology bearing the heading Laboratory Investigation, 76(1):36A, entitled "Cervical Neoplasm Detected by MN Expression in Pap Smears of Atypical Glandular Cells of Undetermined Significant (AGUS)", Jan. 1997, Liao et al.

* cited by examiner

*Primary Examiner*—Karen A. Canella

(57) ABSTRACT

Determining the presence of cancerous or pre-cancerous cervical lesions from ASCUS-diagnosed Pap smear cells by observing the distribution of MN/CA9 antigen expressed on atypical or normal cells and diagnosing (a) significant lesions when MN/CA9 antigen is observed on atypical cells, (b) low grade lesions when MN/CA9 antigen is absent from atypical cells but is present on normal endocervical cells, and (c) a benign condition when MN/CA9 antigen is absent from both atypical cells and normal endocervical cells.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 3 and 5 is confirmed.

Claims 2 and 4 are determined to be patentable as amended.

2. The method of claim 1 wherein said Pap smear cells [that] have been sub-categorized as ASCUS-favor reactive, ASCUS-not otherwise specified (NOS), [and] *or* ASCUS-favor SIL, *and wherein the absence of MN/CA9 detection on Pap smear cells that have been sub-categorized as ASCUS-favor reactive or NOS further confirms a benign condition*.

4. The method of claim 1, wherein said [expression] *MN/CA9 antigen* is detected by immunohistochemistry.

* * * * *